United States Patent [19]
Pischel et al.

[11] Patent Number: 5,863,939
[45] Date of Patent: Jan. 26, 1999

[54] CREATINE ASCORBATES AND A METHOD OF PRODUCING THEM

[75] Inventors: Ivo Pischel, Tacherting; Stefan Weiss, Trostberg; Christian Gloxhuber, Bernau; Bernd Mertschenk, Tacherting, all of Germany

[73] Assignee: SKW Trostberg Aktiengesellschaft, Trostberg, Germany

[21] Appl. No.: 898,512

[22] Filed: Jul. 22, 1997

[30] Foreign Application Priority Data

Feb. 26, 1997 [DE] Germany .................. 197 07 694.7

[51] Int. Cl.$^6$ .................................................. A61K 31/34
[52] U.S. Cl. .......................................... 514/474; 549/316
[58] Field of Search ............................. 514/474; 549/316

[56] References Cited

U.S. PATENT DOCUMENTS

| | | | |
|---|---|---|---|
| 4,590,067 | 5/1986 | Meisner | 424/54 |
| 4,647,453 | 3/1987 | Meisner | 424/54 |

FOREIGN PATENT DOCUMENTS 2313544  12/1997  United Kingdom .
9604240  2/1996  WIPO .

OTHER PUBLICATIONS

Chemical Abstracts 83: 163661u (1975).

*Primary Examiner*—Amelia Owens
*Attorney, Agent, or Firm*—Fulbright & Jaworski, LLP.

[57] ABSTRACT

Creatine ascorbates are described which have the general formula (I)

$$(\text{creatine})_z(\text{ascorbate})_y(H_2O)_n \qquad (I)$$

where
   $z=1$ to 100
   $y=1$ to 100 and
   $n=0$ to 20.

These creatine ascorbates, which can be produced by way of the relatively simple reaction of creatine with ascorbic acid, can be used for enhancing muscular development and strength in the field of sport, as prophylactics against and for the treatment of conditions of oxygen deficit (ischemia) and as immune system stimulants in the field of health, for the treatment of muscular atrophy and as food supplements.

18 Claims, No Drawings

CREATINE ASCORBATES AND A METHOD OF PRODUCING THEM

This patent application relates to creatine ascorbates and their production, the creatine ascorbates being anhydrous or hydrated salts of ascorbic acid and creatine as well as mixtures of these salts with creatine or ascorbic acid.

Ascorbic acid (L-(+)-ascorbic acid, vitamin C, L-3-keto-threo-2-hexuronic acid-γ-lactone, (R)-5-[(S)- 1,2-dihydroxy-ethyl]-3,4-dihydroxy-5H-furan-2-one) is an essential dietary component for the maintenance of human health. It is a well known fact that ascorbic acid and its salts (ascorbates) have valuable physiological, prophylactic and therapeutic properties for the treatment of various diseases. Since the discovery of the most serious vitamin-C deficiency disease, scurvy, and of ascorbic acid's ability to cure it, many interesting effects of this compound have been described.

The most important property of ascorbic acid is its reversible oxidation to dehydro-L-ascorbic acid, which is essential for its physiological effect as an antioxidant. Together with other antioxidants such as carotenes, glutathiones and vitamin E, ascorbic acid acts as a scavenger for free radicals and oxidizing species of oxygen. In addition, ascorbic acid is able to regenerate vitamin E. The antioxidant effect of ascorbic acid leads to activation of the immune system and reduces the risk of cancer. Ascorbic acid has a positive influence on cholesterol metabolism, which leads to a reduction in vascular and, in particular, cardiovascular diseases. It has important functions as an enzyme stimulant or cofactor of oxygenases, which, among other things, bring about the synthesis of dopamine and carnitine. Vitamin C is moreover recommended for the treatment of anaemia, since it promotes the absorption of iron contained in food (cf. Ullmann's Encyclopedia of Industrial Chemistry, 5th ed., 1996, vol. A 27, p. 547–559).

Creatine occurs in muscle and nervous tissue (especially in the CNS), and in the form of its secondary metabolite, phosphocreatine, represents an energy reserve for muscle and brain. In the nervous and cardiac muscle tissue creatine appears to have a prophylactic and therapeutic effect in cases of ischemia resulting for instance from infarcts or pre- or perinatal conditions of oxygen deficit.

Creatine is not only an endogenous substance and a valuable food supplement but also has valuable therapeutic properties. It has been known for over a hundred years as a muscular substance and serves as a source of energy for the muscle. It was shown in a series of scientific studies that the intake of creatine can lead to an increase in muscular tissue and muscular performance.

There are also scientific findings which indicate that the pancreas releases more insulin under the influence of creatine. Insulin promotes the uptake of glucose and amino acids by muscle cells and stimulates protein synthesis. Insulin also lowers the rate of protein catabolism.

The prophylactic, therapeutic or dietetic use of creatine in the most varied of application forms (oral, intravenous etc.) necessitates good bioavailablity, which in turn means high solubility in water. This requirement is not sufficiently fulfilled in the case of creatine, which, as an amino-acid derivative, is present in the form of an internal salt.

The object of this invention was thus to develop forms of creatine which are of particular physiological value and at the same time are highly soluble in water and have a sufficiently long shelf life.

This object was established according to the invention by providing creatine ascorbates having the formula (I)

where
z=1 to 100, preferably 1 to 5
y=1 to 100, preferably 1 to 5 and
n =0 to 20, preferably 0 to 2

Depending on the stoichiometric requirements, creatine is present in the compounds of formula (I) in uncharged or cationic form and ascorbate as ascorbic acid or as anion.

Surprisingly, it was found that the creatine ascorbates of the invention have a long shelf life, although the hitherto known salts of creatine decompose to form creatinine. Since creatine occurs as an internal salt and is only a relatively weak base, it was not predictable that stable creatine salts can be formed with acid enols. According to the prior art, namely, only creatine salts of strong di and tricarboxylic acids were known hitherto (cf. WO 96/04 240), and these are strongly acidic hydrogen salts.

The creatine ascorbates of the invention, having the general formula (I), contain the physiologically particularly valuable creatine cation of formula (II) and the ascorbate ion of formula (III).

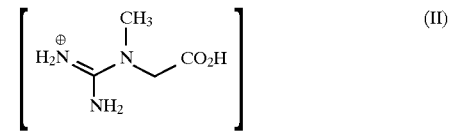

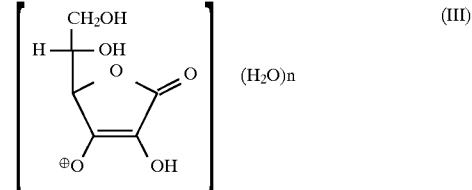

The creatine ascorbates according to the invention comprise salts which preferably contain the creatine cation and the ascorbate anion in a molar ratio of 1:1 or a molar ratio of approximately 1:1 . The creatine ascorbates of the invention can moreover also be mixtures of these salts with creatine or ascorbic acid.

The creatine ascorbates of the invention can be produced by way of the relatively simple reaction of creatine with ascorbic acid in the temperature range from −10° to 90° C., preferably in the temperature range from 10° to 30° C. The creatine and ascorbic acid are reacted here in a molar ratio of 100:1 to 1:100, preferably one of 5:1 to 1:5 . For this reaction creatine may be used in the anhydrous form, as monohydrate or as wet product. The ascorbic acid may be used as anhydrous acid or in the form of an aqueous solution.

The reaction may be carried out in the presence or absence of a solvent or diluting agent. A broad range of organic solvents is suitable as solvent or diluting agent. Preference is given to alcohols (such as methanol, ethanol, isopropanol or cyclohexanol), ethers (such as diethyl ether, tetrahydrofuran, 1,4-dioxane or ethylene dimethyl ether), ketones (such as acetone, methyl ethyl ketone or cyclohexanone), esters (such as methyl acetate, ethyl acetate or ethyl formate) or aliphatic (pentane, hexane, cyclohexane) and aromatic (toluol) hydrocarbons or mixtures thereof. The reaction can be carried out using customary technical apparatus such as mixers, blade driers and agitating vessels.

The creatine ascorbates with water of crystallization are obtained by adding water during or after the reaction of ascorbic acid with creatine and/or by using aqueous creatine and/or aqueous ascorbic acid. The scope of this invention also allows for the addition—during or after production of the creatine ascorbates—of other substances too, such as pharmaceutical formulation additives, vitamins, mineral substances, trace elements, carbohydrates such as glucose, dextrose, or maltose and amino acids such as L-carnitine or other food supplements.

The subject matter of the invention thus also comprises physiologically compatible compositions which contain creatine ascorbate and at least one additional, physiologically compatible substance selected from the group comprising pharmaceutical adjuvants or carriers, vitamins, mineral substances, carbohydrates, amino acids or other food supplements.

By virtue of their valuable physiological properties, long shelf life, high solubility in water and high bioavailability, the creatine ascorbates of the invention are excellently suited for therapeutic applications in medicine and as food supplements, exhibiting not only the known valuable biological and medical properties of ascorbates and of creatine but surprisingly, in addition the these, also marked synergistic effects.

The creatine ascorbates of the invention are particularly suitable in this context for enhancing muscular development and strength in the field of sport, as prophylactics against and for the treatment of conditions of oxygen deficit (ischemia) and as immune system stimulants in the field of health, in the treatment of muscular atrophy and as a food supplement.

The following examples serve to explain the invention in more detail.

EXAMPLES

Example 1

17.6 g (0.1 mol) L-ascorbic acid and 14.9 g (0.1 mol) creatine monohydrate are suspended at room temperature in 100 ml of ethyl acetate. The mixture is agitated for four hours, then the white, finely crystalline product is separated out by filtering and washed twice with 25 ml of ethyl acetate. It is then dried for four hours at 50° C. in a vacuum-drying chamber. The yield is almost quantitative (>99%). The creatine ascorbate (1:1) melts at 134° to 136° C and decomposes (capillary).

$C_{10}H_{17}N_3 \ O_8 \times 0.28 \ H_2O$ , calculated: C 38.47%, H 5.68%, N 13.46%; found: C 38.40%, H 5.72%, N 13.49%; IR (KBr) [1/cm]: 703, 756, 821, 870, 983, 1027, 1113, 1306, 1395, 1617, 1694, 2362, 2799, 3074, 3343, 3408, 3525; $^1$H-NMR ($D_2O$, 300 MHz): δ=2.98 (s, 3H, Me-Kr), 3.69 (s, 2H, $CH_2$-AS), 3.92 (s, 2H, $CH_2$-Kr), 4.00 (t, 1H, CHOH-AS); 4.83 (s, 1H, CH-AS).

Example 2

8.8 g (0.05 mol) L-ascorbic acid and 6.6 g (0.05 mol) creatine are suspended at room temperature in 50 ml of tetrahydrofuran. The mixture is agitated for 2 hours, then the finely crystalline product separated out by filtering and washed twice with 20 ml of tetrahydrofuran. It is then dried for four hours at 50° C. in a vacuum-drying chamber. The yield is 95.4%. The creatine ascorbate (1:1) melts at 133° to 135° C. and decomposes (capillary).

Example 3

17.62 g (0.1 mol) L-ascorbic acid and 6.56 g (0.05 mol) creatine are suspended at room temperature in a mixture of 75 ml of ethyl acetate and 75 ml of ethanol. The mixture is agitated for 2 hours, then the white crystalline product separated out by filtering and washed twice with 20 ml of the solvent mixture. It is dried at 50° C. in a vacuum-drying chamber until its weight remains constant. The yield is 94.0% The creatine ascorbate (1:2) melts at 128° to 131° C. and decomposes (capillary).

Example 4

8.8 g (0.05 mol) L-ascorbic acid and 14.9 g (0.1 mol) creatine monohydrate are suspended at 30° C. in 75 ml of isopropanol and the mixture agitated for 2 hours. Then the white, finely crystalline product is separated out by filtering and washed twice with isopropanol. It is dried at 50° C. in a vacuum-drying chamber. The yield is 86.5%. The creatine ascorbate (2:1) melts at 129° to 132° C. and decomposes (capillary).

We claim:

1. Creatine ascorbates with the general formula (I)

$$(\text{creatine})_z(\text{ascorbate})_y(H_2O)_n \qquad (I)$$

where z=1 to 100 y=1 to 100 and n=0 to 20.

2. Creatine ascorbates as claimed in claim 1, wherein z=1 to 5, y=1 to 5 and n=0 to 2.

3. A method of producing the creatine ascorbates of claim 1 comprising reacting creatine and ascorbic acid in a molar ratio of 100:1 to 1:100, at a temperature from −10° to 90° C.

4. The method of claim 3 wherein said temperature is between 10° and 30° C.

5. The method of claim 3, wherein the molar ratio of creatine to ascorbic acid is 5:1 to 1:5.

6. The method of claim 3 comprising carrying out said reaction in the presence of a solvent.

7. The method of claim 6, wherein said solvent is selected from the group consisting of an alcohol, an ether, a ketone, an ester an aliphatic hydrocarbon and an aromatic hydrocarbon.

8. A physiologically compatible composition comprising the creatine ascorbate of claim 1 and at least one additional, physiologically compatible substance selected from the group consisting of a pharmaceutical adjuvant a carrier, a vitamin, a mineral substance, a carbohydrate, and an amino acid.

9. A method for enhaning muscle development and strength in the field of sport comprising administering a sufficient amount of the creatine ascorbates of claim 1 to enhance muscle development and strength in the field of sport to a patient in need thereof.

10. The method of claim 4, comprising carrying out said reaction in the presence of a solvent.

11. The method of claim 5, comprising carrying out said reaction in the presence of a solvent.

12. The method of claim 10, wherein said solvent is an alcohol, an ether, a ketone, an ester, an aliphatic hydrocarbon or an aromatic hydrocarbons.

13. The method of claim 11, wherein said solvent is an alcohol, an ether, a ketone, an ester, an aliphatic hydrocarbon or an aromatic hydrocarbons.

14. The physiologically compatible composition of claim 8, wherein Z is 1 to 5, Y is 1 to 5, and n is 0 to 2.

15. A method for prophylaxis of conditions of oxygen deficit comprising administering to a patient a sufficient amount of the creatine ascorbates of caim 1 to provide prophylaxis for conditions of oxygen deficit.

16. A method of treating conditions of oxygen deficit comprising administering to a patient an amount of the creatine ascorbates of claim 1 sufficient to treat the oxygen deficit disorder of the patient.

17. A method of stimulating the immune system comprising administering to a patient an amount of the creatine ascorbates of claim 1 sufficient to stimulate the immune system of the patient.

18. A method of treating muscular atrophy comprising administering to a patient a sufficient amount of the creatine ascorbates of claim 1 to treat the muscular atrophy.

* * * * *